United States Patent
Miyazawa et al.

[11] Patent Number: 5,948,318
[45] Date of Patent: *Sep. 7, 1999

[54] LIQUID CRYSTAL COMPOSITION AND LIQUID CRYSTAL DISPLAY DEVICE

[75] Inventors: Kazutoshi Miyazawa; Shuichi Matsui; Tomoyuki Kondo; Takashi Kato; Yasuko Sekiguchi; Etsuo Nakagawa, all of Chiba, Japan

[73] Assignee: Chisso Corporation, Osaka-fu, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/698,456

[22] Filed: Aug. 15, 1996

[30] Foreign Application Priority Data

Sep. 11, 1995 [JP] Japan .................. 7-258185

[51] Int. Cl.$^6$ .................. C09K 19/30; C09K 19/12; C09K 19/20; G02F 1/13
[52] U.S. Cl. .................. 252/299.63; 252/299.66; 252/299.67; 349/182
[58] Field of Search .................. 252/299.66, 299.63, 252/299.67; 349/182

[56] References Cited

U.S. PATENT DOCUMENTS

| | | | |
|---|---|---|---|
| 5,032,313 | 7/1991 | Goto et al. | 252/299.63 |
| 5,286,411 | 2/1994 | Rieger et al. | 252/299.63 |
| 5,308,541 | 5/1994 | Hittich et al. | 252/299.63 |
| 5,329,644 | 7/1994 | Goulding et al. | 252/299.66 |
| 5,350,535 | 9/1994 | Rieger et al. | 252/299.63 |
| 5,389,389 | 2/1995 | Rieger et al. | 252/299.01 |
| 5,397,505 | 3/1995 | Rieger et al. | 252/299.67 |
| 5,409,637 | 4/1995 | Rieger et al. | 252/299.63 |
| 5,468,421 | 11/1995 | Matsui et al. | 252/299.63 |
| 5,496,499 | 3/1996 | Poetsch et al. | 252/299.66 |
| 5,520,846 | 5/1996 | Plach et al. | 252/299.63 |
| 5,565,140 | 10/1996 | Hittich et al. | 252/299.63 |
| 5,618,466 | 4/1997 | Tomi et al. | 252/299.63 |

*Primary Examiner*—C. H. Kelly
*Attorney, Agent, or Firm*—Wenderoth, Lind & Ponack, L.L.P.

[57] ABSTRACT

Liquid crystal compositions which have a low threshold voltage, excellent miscibility at low temperatures, and a wide range of a nematic phase while satisfying various characteristics required of liquid crystal compositions for active matrix mode liquid crystal display devices. The compositions contain, as a first component, at least one compound expressed by any one of formulas

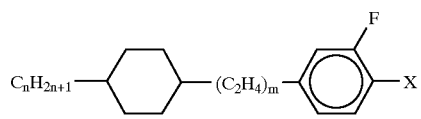

-continued

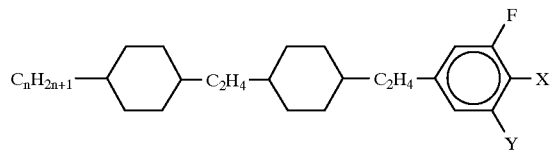

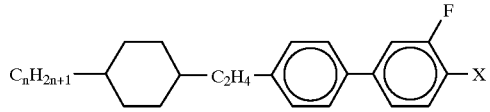

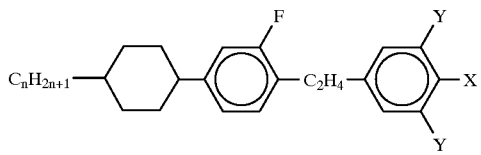

and as a second component, at least one compound expressed by any one of formulas

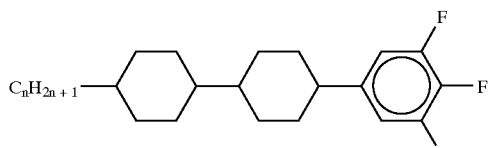

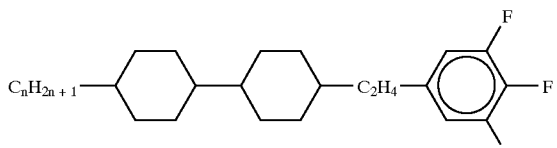

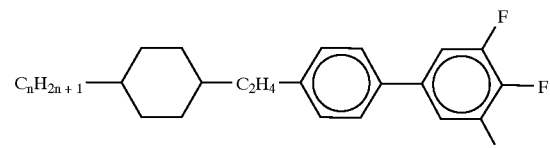

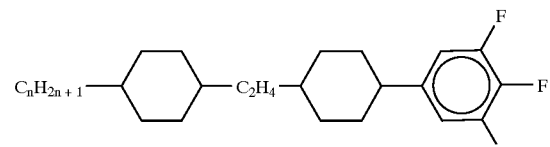

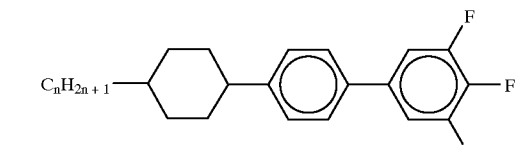

wherein each of the formulas, X represents $CF_3$ or $OCF_3$, each Y represents, independently of each other, a hydrogen or fluorine atom, m is 1 or 2, and n is an integer or 1 to 10.

13 Claims, No Drawings

LIQUID CRYSTAL COMPOSITION AND LIQUID CRYSTAL DISPLAY DEVICE

TECHNICAL FIELD

The present invention relates to a novel nematic liquid crystal composition. More specifically, the present invention relates to a liquid crystal composition for an active matrix mode liquid crystal display device and a liquid crystal display device comprising the liquid crystal composition.

BACKGROUND ART

Liquid crystal display devices (LCD) have been produced by filling a liquid crystal composition in a sealed cell formed between two substrates provided with transparent electrodes. LCD have been practically used in various modes such as twist nematic (TN) mode, super twist nematic (STN) mode, and thin-film transistor (TFT) mode since their electric power consumption is small compared with CRT (cathode ray tube display) and since downsizing and weight-lightening are possible. Among the modes, active matrix LCD (AM-LCD) such as TFT have been watched as a prospective winner of flat display accompanied with the progress in actualization of colored display and fine picture image in AM-LCD.

Following characteristics are required of the liquid crystal compositions for AM-LCD:

1) Proper optical anisotropy (Δn) can be produced depending on cell thickness.
2) Voltage holding ratio (VHR) is high in order to maintain a high contrast of LCD.
3) Proper threshold voltage ($V_{th}$) can be actualized depending on driving circuit.
4) Range of nematic liquid crystal phase is wide depending on application environment (wide range).

AM-LCD have adopted for their driving a TN display mode in which the molecular orientation of a liquid crystal composition filled between an upper and a lower substrate is twisted by 90°. TN display mode has a problem that the coloring of liquid crystal cell is caused due to interference when voltage is not applied. In order to avoid the coloring and to obtain an optimum contrast, the product (Δn·d) of Δn and cell thickness d ($\mu$m) must be established to a certain value, for example, to a 0.5 $\mu$m. Since such restriction exists, a main current of Δn of liquid crystal compositions for TFT currently used in practice is generally about 0.07 to about 0.11 and particularly 0.08 to 0.10 for 1st. Min. system.

In recent years, the development of LCD with a purpose of providing LCD for portable type is active as seen from the appearance of small size and light weight notebook type personal computers. With respect to such portable LCD, the reduction of production cost is desired in addition to further weight-lightening and downsizing whereas there are many restrictions in the aspect of driving electric power. As a means to meet such demand, liquid crystal materials of small electric power consumption and low $V_{th}$ are called to mind, and the development of such materials is expected.

Accompanied with the appearance of the portables, exploration for LCD intended for outdoor use has come to be attempted. In order to withstand outdoor use, liquid crystal compositions are considered to be necessary to exhibit a nematic phase even in a range beyond the temperature range of application environment. From such viewpoint, liquid crystal compositions having a nematic-isotropic phase transition temperature (clearing point $T_{NI}$) of 60° C. or higher and smectic-nematic phase transition temperature ($T_{SN}$) of lower than −20° C. have become a main stream of liquid crystal compositions for TFT currently used in practice.

In order to respond to such demand, various types of liquid crystalline compounds and liquid crystal compositions containing the compounds have been developed. For instance, Laid-open Japanese Patent Publication No. Hei 2-233626 has disclosed in its Application Example 2 a composition comprising 15% by weight of a trifluoro compound having a comparatively large dielectric anisotropy (Δε) and 85% by weight of a difluoro compound. However, this composition has defects that $V_{th}$ is high, the miscibility of the components in the composition are deteriorated particularly at low temperatures, and nematic phase range is narrow.

WO 94/03558 has disclosed compositions comprising a trifluoro compound and a difluoro compound. However, the compositions disclosed in its Examples 1 and 2 have such a low clearing point as lower than 50° C. and have a Δn of lower than 0.06, and thus the compositions are short of practical utility.

Liquid crystal compositions are diligently being studied depending on various purposes as discussed above, but still they are not sufficient. Thus, it is a present situation that new improvements are all the time demanded.

DISCLOSURE OF THE INVENTION

An object of the present invention is to dissolve the problems in the prior art mentioned above and to provide a liquid crystal composition which has particularly a low $V_{th}$, is excellent in miscibility at low temperatures, and has a wide range of a nematic phase while satisfying various characteristics required of liquid crystal compositions for AM-LCD.

As a result of the investigation by the present inventors to achieve the objects mentioned above, the present invention as described below has been accomplished.

BEST MODE FOR CARRYING OUT THE INVENTION

Liquid crystal composition of the present invention is characterized by containing, as a first component, at least one compound selected from the group consisting of the compounds expressed by any one of formulas (I-1) to (I-4)

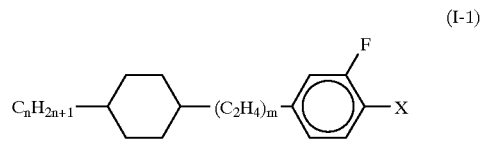

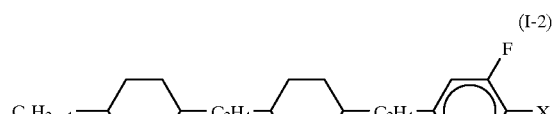

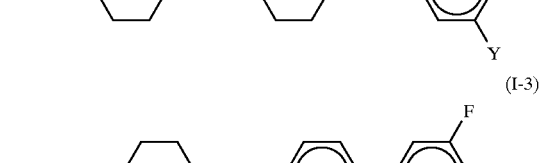

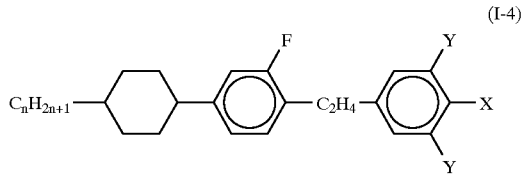
(I-4)

and containing, as a second component, at least one compound selected from the group consisting of the compounds expressed by any one of formulas (II-1) to (II-5)

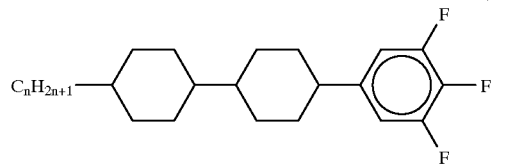
(II-1)

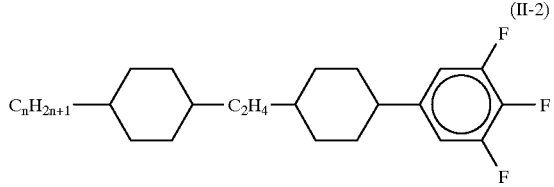
(II-2)

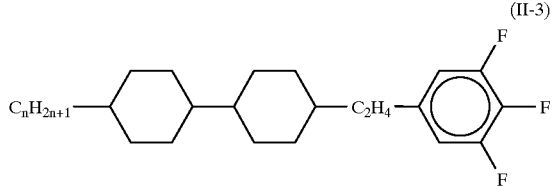
(II-3)

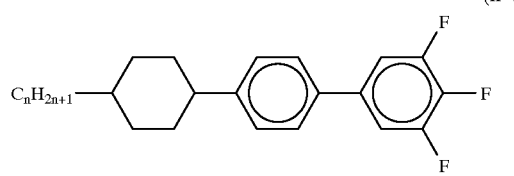
(II-4)

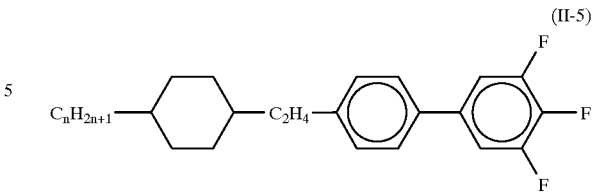
(II-5)

in each of the formulas mentioned above, X represents $CF_3$ or $OCF_3$, Y represents or Ys independently with each other represent hydrogen atom or fluorine atom, m is 1 or 2, and n is an integer of 1 to 10.

In the liquid crystal compositions of the present invention, the ratio of the amount of the first component to the amount of the second component in the total amount of the first component and the second component is preferably 3 to 50% by weight (first component) to 50 to 97% by weight (second component). Total amount of the first component and the second component is preferably 60 to 100% by weight based on the total amount of liquid crystal composition.

Liquid crystal composition of the present invention may further contain a compound of a first group expressed by the following formula (III), a compound of a second group expressed by formula (IV-1) or (IV-2), a compound of a third group expressed by formula (V-1) or (V-2), or a compound of fourth group expressed by formula (VI-1) or (VI-2).

Compound of the first group:

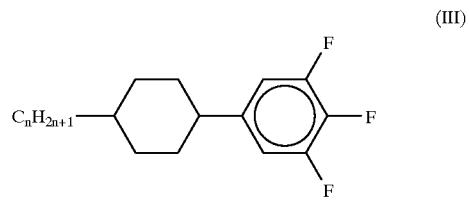
(III)

wherein n is an integer of 1 to 10.

Compound of the second group:

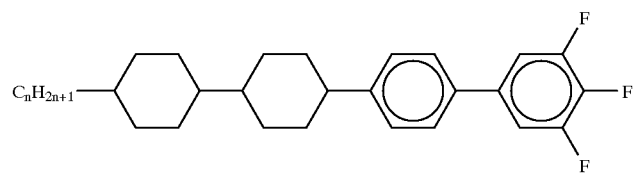
(IV-1)

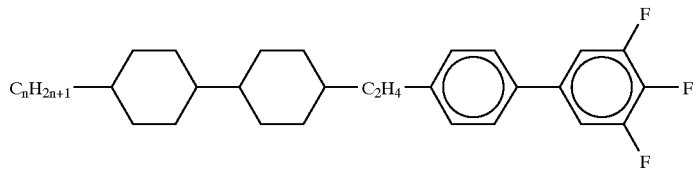
(IV-2)

wherein n is an integer of 1 to 10.
Compound of the third group:

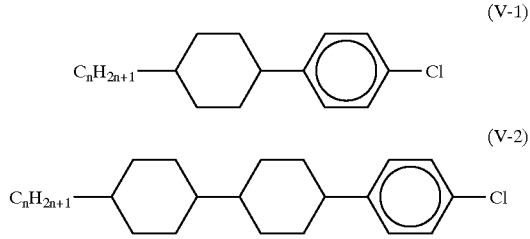
(V-1)

(V-2)

wherein n is an integer of 1 to 10.
Compound of the fourth group:

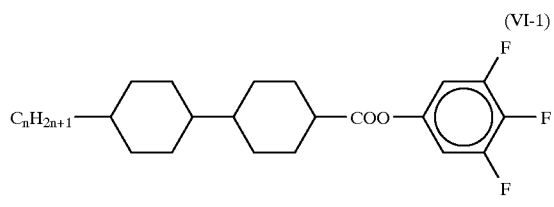
(VI-1)

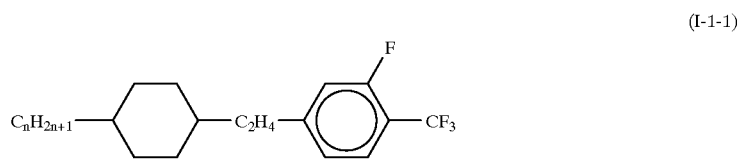
(VI-2)

wherein n is an integer of 1 to 10.

By using these liquid crystal compositions of the present invention, liquid crystal display devices which satisfy the objects of the present invention can be obtained.

As preferable examples of the first component used in the liquid crystal compositions of the present invention, there can be mentioned compounds expressed by any one of formulas (I-1-1) to (I-1-3) with the compounds of formula (I-1); compounds expressed by any one of formulas (1-2-1) to (I-2-4) with the compounds of formula (I-2); compounds of formula (I-3-1) or (I-3-2) with the compounds of formula (I-3); and compounds expressed by any one of formulas (1-4-1) to (I-4-6) with the compounds of formula (I-4).

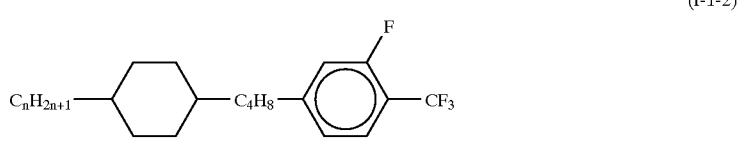
(I-1-1)

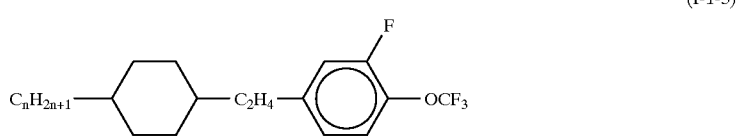
(I-1-2)

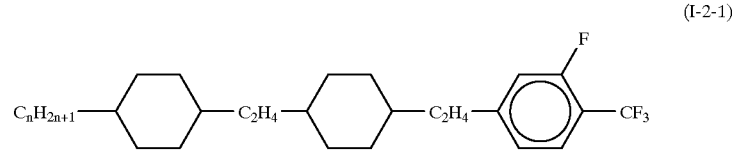
(I-1-3)

(I-2-1)

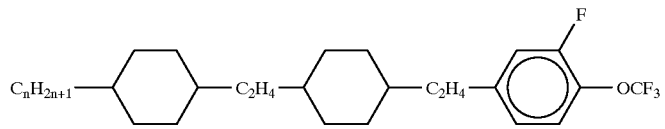
(I-2-2)
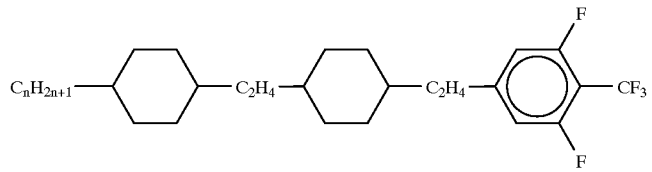
(I-2-3)
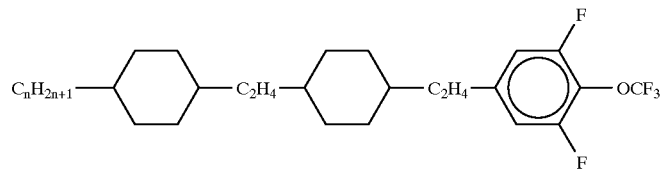
(I-2-4)
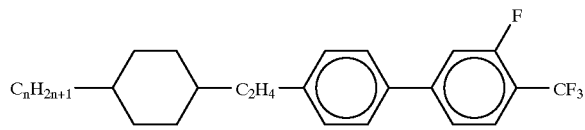
(I-3-1)
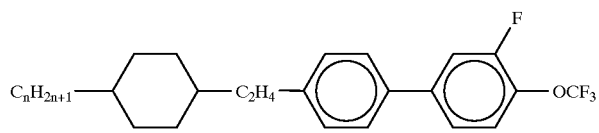
(I-3-2)
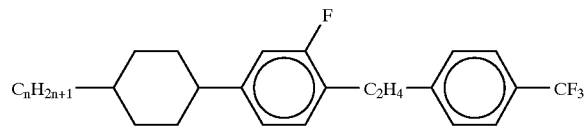
(I-4-1)
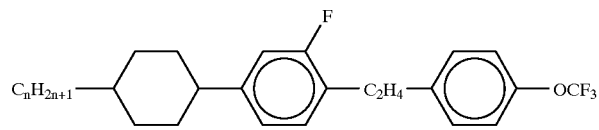
(I-4-2)
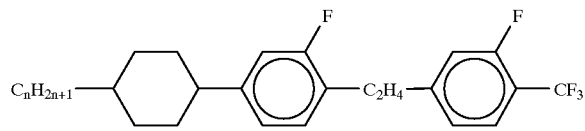
(I-4-3)
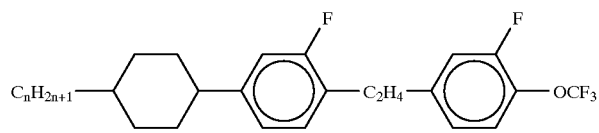
(I-4-4)

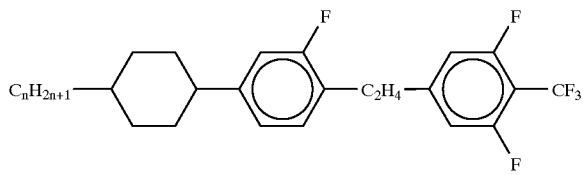

(I-4-5)

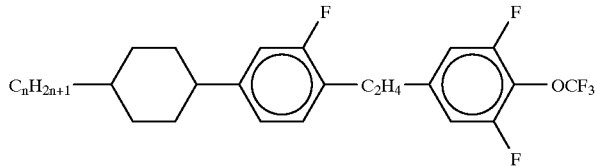

(I-4-6)

in each of the formulas shown above, n is an integer of 1 to 10.

Among these compounds, particularly the ones expressed by any one of formulas (I-1-1), (I-1-2), (I-2-2), (I-2-3), (I-2-4), (I-3-1), (I-3-2), (I-4-4), and (I-4-6) are preferably used.

Since the compounds of the first component have a $\Delta\epsilon$ generally in the range of 7 to 16 and are excellent in heat stability and chemical stability, the compounds of the first component particularly assume the role of lowering $V_{th}$ of liquid crystal compositions for TFT.

Their content is generally 3 to 50% by weight and preferably 5 to 35% by weight based on the total amount of the first component and the second component. When the content is less than 3% by weight, effects such as a low $V_{th}$ in the objects of the present invention come to be hardly achieved. Conversely, when the content exceeds 50% by weight, the viscosity of liquid crystal compositions becomes high and the miscibility at low temperatures is deteriorated both of which are unpreferable in the present invention.

Any of the compounds expressed by any one of the formulas (II-1) to (II-5) for the second component and the compounds of the first, the second, and the fourth group is a trifluoro compound. As will be clear from the Laid-open Japanese Patent Publication No. Hei 2-233626 mentioned above, those compounds have a $\Delta\epsilon$ in the range of about 7 to about 12 and are excellent in heat stability and chemical stability, and thus they are well known as compounds for low voltage TFT (R. Tarao et al., SID 94 Digest, p 233).

Among them, the compounds of the second component have a $T_{NI}$ in the range of about 50 to about 100° C. and thus they are most suitable as base compound of liquid crystal compositions for low voltage TFT.

Content of the second component is generally 50 to 97% by weight and preferably 65 to 95% by weight based on the total amount with the first component. When the content is less than 50% by weight, the miscibility of liquid crystal compositions is sometimes deteriorated particularly at low temperatures. Conversely, when the content exceeds 97% by weight, the effect of lowering the $V_{th}$ of liquid crystal compositions comes to be hardly achieved.

Among the compounds of the first to the fourth groups which can be further added to the liquid crystal compositions of the present invention, the compounds of the first group expressed by formula (III) are bicyclic trifluoro compounds and particularly assume the role of lowering $V_{th}$.

Their content is generally less than 15% by weight and preferably less than 10% by weight to avoid an excessive lowering of $T_{NI}$ of liquid crystal compositions.

Next, the compounds of the second group expressed by formula (IV-1) or (IV-2) are tetracyclic trifluoro compounds and particularly assume the role of raising $T_{NI}$ of liquid crystal compositions.

However, since they have a tetracyclic structure, they sometimes raise $V_{th}$ and deteriorate miscibility at low temperatures when used in a large amount. Accordingly, their content is generally less than 20% by weight and preferably less than 10% by weight based on the total amount of liquid crystal composition.

Compounds of the third group expressed by formula (V-1) or (V-2) are bi- or tricyclic compounds containing chlor (Cl) and mainly assume the role of reducing the viscosity of liquid crystal compositions. Since these compounds have a small $\Delta\epsilon$ of 4 to 5, $V_{th}$ of liquid crystal compositions is sometimes heightened when the compounds were used in a large amount. Accordingly, their content is generally less than 30% by weight and preferably less than 25% by weight based on the total amount of liquid crystal-composition.

Compounds of the fourth group expressed by formula (VI-1) or (VI-2) are ester type trifluoro compounds and particularly assume the role of lowering $V_{th}$ of liquid crystal compositions.

However, they sometimes deteriorate miscibility of liquid crystal compositions at low temperatures when used in a large amount. Accordingly, their content is generally less than 20% by weight and preferably less than 15% by weight based on the total amount of liquid crystal compositions.

Liquid crystal compositions of the present invention may contain other compounds with the purpose of achieving the objects of the present invention, for example, to improve $V_{th}$, miscibility at low temperatures, and the range of a nematic phase, in addition to the compounds of the first group to the fourth group mentioned above.

Liquid crystal compositions of the present invention are produced by methods conventional in the art, for instance, by a method in which various components are dissolved in each other at a high temperature, and a method in which various components are dissolved in an organic solvent to mix and then the solvent is distilled off under a reduced pressure.

Also, if necessary, the liquid crystal compositions of the present invention are improved to optimize depending on the applications intended, by adding a suitable additive. Such additive is well known in the art and described in detail in literatures. Usually, a chiral dopant or like is added to cause a helical structure of liquid crystal to adjust a required twisting angle and to avoid reverse-twist.

Further, the liquid crystal compositions of the present invention can be used as ones for guest-host (GH) mode when a dichroic dye such as merocyanine type, styryl type, azo type, azomethine type, azoxy type, quinophthalone type, anthraquinone type, and tetrazine type was added.

Liquid crystal compositions of the present invention can be used even as ones for polymer dispersion type liquid crystal display devices (PDLCD) typified by a NCAP which is prepared by forming a nematic liquid crystal into a microcapsule or typified by a polymer network liquid crystal display devices (PNLCD) which is prepared by forming a polymer of three-dimensional network structure in a liquid crystal; for electrically controlled birefringence (ECB) mode; and for dynamic scattering (DS) mode.

According to the present invention, liquid crystal compositions can be provided which particularly have a low $V_{th}$, are excellent in miscibility at low temperatures, and have a wide range of a nematic phase while satisfying various characteristics required of the liquid crystal compositions for AM-LCD.

Now, the present invention will be described in more detail with reference to Examples and Comparative Examples. However, it should be understood that the present invention is by no means restricted by such specific Examples and Comparative Examples.

In the following Examples, compounds are designated according to the understanding shown in Table 1 below. That is, left side terminal group is expressed by n—, nO—, nOm—, Vn—, nVm—, or nVmVk— (n, m, and k are an integer of 1 or more); bonding group is expressed by 2, E, T, V, CF2O, or OCF2; ring structure is expressed by B, B(F), B(F,F), H, Py, D, or Ch; and right side terminal group is expressed by —F, —CL, —C, —CF3, —OCF3, —OCF2H, —n, —On, —EMe, —nV, or —mVn (in which n and m are an integer of 1 or more). The % showing the content of each compound means % by weight unless otherwise specified.

Characteristics data of liquid crystal compositions were shown by $T_{NI}$ (clearing point), $T_{SN}$ (smectic-nematic phase transition point), η20 (viscosity at 20° C.), An (optical anisotropy at 25° C.), Δε (dielectric anisotropy at 25° C.), $V_{th}$ (threshold voltage at 20° C.), and VHR at 25° C. (voltage holding ratio determined by "Area Method"). $T_{SN}$ mentioned above was judged by liquid crystal phase after a liquid crystal composition was left in each of freezers kept at 0° C., −10° C., −20° C., or −30° C. for 30 days.

TABLE 1

| Left side terminal group | Symbol | Bonding group | Symbol |
| --- | --- | --- | --- |
| $C_nH_{2n+1}$— | n- | —$CH_2CH_2$— | 2 |
| $C_nH_{2n+1}$O— | nO— | —COO— | E |
| $C_nH_{2n+1}OC_mH_{2m}$— | nOm- | —C≡C— | T |
| $CH_2=CHC_nH_{2n}$— | Vn- | —CH=CH— | V |
| $C_nH_{2n+1}CH=CHC_mH_{2m}$— | nVm- | —$CF_2O$— | CF2O |
| $C_nH_{2n+1}CH=CHC_mH_{2m}CH=CHC_kH_{2k}$— | nVmVk- | —$OCF_2$— | OCF2 |

| Ring structure | Symbol | Right side terminal group | Symbol |
| --- | --- | --- | --- |
|  | B | —F<br>—Cl | —F<br>—CL |
| 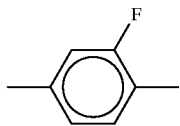 | B(F) | —CN | —C |
| 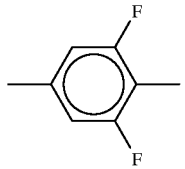 | B(F,F) | —$CF_3$<br>—$OCF_3$ | —$CF_3$<br>—$OCF_3$ |
|  | H | —$OCF_2H$ | —OCF2H |
| 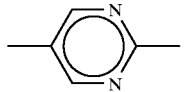 | Py | —$C_nH_{2n+1}$<br>—$OC_nH_{2n+1}$ | -n<br>—On |

TABLE 1-continued

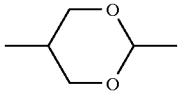

| | D | —COOCH$_3$ | —EMe |

| | Ch | —C$_n$H$_{2n}$CH=CH$_2$ | -nV |
| | | —C$_m$H$_{2m}$CH=CHC$_n$H$_{2n+1}$ | -mVm |

COMPARATIVE EXAMPLE 1

Application Example 2 in the Laid-open Japanese Patent Publication No. Hei 2-233626 mentioned above has disclosed the liquid crystal composition comprising the following compounds:

| | | |
|---|---|---|
| 3-HHB(F,F)—F | | 15.0% |
| 2-HHB(F)—F | | 28.4% |
| 3-HHB(F)—F | | 28.3% |
| 5-HHB(F)—F | | 28.3% |

Characteristics of the composition were determined and the results were as follows:

$T_{NI}$=110.7° C.
$T_{SN}$<0° C.
$\eta 20$=25.0 mPa·s
$\Delta n$=0.077
$V_{th}$=2.32 V
VHR=98.8%

As will be clear from the results mentioned above, it can be understood that the liquid crystal composition of Comparative Example 1 has a high $V_{th}$. Besides, it is not good in miscibility at low temperatures ($T_{SN}$ is high).

COMPARATIVE EXAMPLE 2

Example 1 in the WO 94/03558 mentioned above has disclosed the liquid crystal composition comprising the following compounds:

| | | |
|---|---|---|
| 7-HB(F,F)—F | | 10.0% |
| 2-HHB(F,F)—F | | 25.0% |
| 3-HHB(F,F)—F | | 35.0% |
| 5-HHB(F,F)—F | | 18.0% |
| 7-HB(F)—F | | 12.0% |

Characteristics of the composition were determined and the results were as follows:

$T_{NI}$=42.9° C.
$T_{SN}$<0° C.
$\eta 20$=22.2 mPa·s
$\Delta n$=0.059
$V_{th}$=1.07 V
VHR=98.7%

As will be clear from the results mentioned above, it can be understood that whereas the liquid crystal composition of Comparative Example 2 has a low $V_{th}$, it has a low $T_{NI}$ (clearing point) and is not good in miscibility at low temperatures ($T_{SN}$ is high). Besides, it exhibits a small $\Delta n$ and thus this composition is insufficient in practical utility.

COMPARATIVE EXAMPLE 3

Example 2 in the WO 94/03558 mentioned in Comparative Example 2 has disclosed the liquid crystal composition comprising the following compounds:

| | | |
|---|---|---|
| 2-HHB(F,F)—F | | 26.0% |
| 3-HHB(F,F)—F | | 26.0% |
| 5-HHB(F,F)—F | | 26.0% |
| 7-HB(F)—F | | 12.0% |
| 5-H2B(F)—F | | 10.0% |

Characteristics of the composition were determined and the results were as follows:

$T_{NI}$=46.0° C.
$T_{SN}$<0° C.
$\eta 20$=21.6 mPa·s
$\Delta n$ 0.058
$V_{th}$=1.17 V
VHR=98.5%

As will be clear from the results mentioned above, it can be understood that whereas the liquid crystal composition of Comparative Example 3 has a low $V_{th}$, it has a low $T_{NI}$ (clearing point) and is not good in miscibility at low temperatures ($T_{SN}$ is high). Besides, it exhibits a small $\Delta n$ and thus this composition is insufficient in practical utility.

EXAMPLE 1

Liquid crystal composition comprising the following compounds was prepared:

| | | |
|---|---|---|
| 5-H2B(F)—CF3 | | 10.0% |
| 3-H2BB(F)—CF3 | | 10.0% |
| 3-H2BB(F)—OCF3 | | 10.0% |
| 3-H2HB(F,F)—F | | 15.0% |
| 4-H2HB(F,F)—F | | 10.0% |
| 5-H2HB(F,F)—F | | 10.0% |
| 3-HHB(F,F)—F | | 10.0% |
| 3-HH2B(F,F)—F | | 15.0% |
| 5-HH2B(F,F)—F | | 10.0% |

Characteristics of the composition were determined and the results were as follows:

$T_{NI}$=69.2° C.
$T_{SN}$<−30° C.
$\eta 20$=26.4 mPa·s
$\Delta n$=0.083
$\Delta \epsilon$=8.1

$V_{th}$=1.76 V

VHR=98.8%

As will be seen from the results mentioned above, the liquid crystal composition of this Example is excellent in miscibility at low temperatures compared with that in Comparative Examples 1 to 3 and has a properly large Δn. Range of a nematic phase is wide ($T_{NI}$ is high) such an extent that causes practically no problem. Besides, $V_{th}$ exhibits a low value, and thus the composition of Example 1 can be understood to have a balanced characteristics as a whole and to be sufficient in practical utility.

EXAMPLE 2

Liquid crystal composition comprising the following compounds was prepared:

| | |
|---|---|
| 3-H2B(F)—CF3 | 5.0% |
| 3-H2HB(F,F)—F | 12.0% |
| 4-H2HB(F,F)—F | 10.0% |
| 5-H2HB(F,F)—F | 10.0% |
| 3-HHB(F,F)—F | 10.0% |
| 4-HHB(F,F)—F | 5.0% |
| 3-HH2B(F,F)—F | 15.0% |
| 5-HH2B(F,F)—F | 10.0% |
| 3-HBB(F,F)—F | 12.0% |
| 5-H2BB(F,F)—F | 11.0% |

Characteristics of the composition were determined and the results were as follows:

$T_{NI}$=71.6° C.

$T_{SN}$<-30° C.

η20=27.1 mPa·s

Δn=0.084

Δε=8.3

$V_{th}$=1.69 V

VHR=98.5%

EXAMPLE 3

Liquid crystal composition comprising the following compounds were prepared:

| | |
|---|---|
| 3-H2BB(F)—CF3 | 10.0% |
| 7-HB(F,F)—F | 4.0% |
| 3-H2HB(F,F)—F | 12.0% |
| 4-H2HB(F,F)—F | 10.0% |
| 5-H2HB(F,F)—F | 10.0% |
| 3-HHB(F,F)—F | 10.0% |
| 4-HHB(F,F)—F | 4.0% |
| 3-HH2B(F,F)—F | 15.0% |
| 5-HH2B(F,F)—F | 13.0% |
| 3-HBB(F,F)—F | 12.0% |

Characteristics of the composition were determined and the results were as follows:

$T_{NI}$=74.5° C.

$T_{SN}$<-30°C.

η20=27.1 mPa·s

Δn=0.085

Δε=8.6

$V_{th}$=1.68 V

VHR=98.6%

EXAMPLE 4

Liquid crystal composition comprising the following compounds was prepared:

| | |
|---|---|
| 3-H2B(F)—CF3 | 5.0% |
| 3-H2H2B(F)—OCF3 | 7.0% |
| 3-H2H2B(F,F)—CF3 | 3.0% |
| 3-HHB(F,F)—F | 8.0% |
| 3-H2HB(F,F)—F | 10.0% |
| 5-H2HB(F,F)—F | 10.0% |
| 3-HH2B(F,F)—F | 10.0% |
| 5-HH2B(F,F)—F | 5.0% |
| 3-HBB(F,F)—F | 10.0% |
| 5-HBB(F,F)—F | 10.0% |
| 3-H2BB(F,F)—F | 8.0% |
| 5-H2BB(F,F)—F | 6.0% |
| 3-HHBB(F,F)—F | 4.0% |
| 3-HH2BB(F,F)—F | 4.0% |

Characteristics of the composition were determined and the results were as follows:

$T_{NI}$=78.8° C.

$T_{SN}$<-30° C.

η20=28.3 mPa·s

Δn=0.094

Δε=9.2

$V_{th}$1.77 V

VHR=98.7%

EXAMPLE 5

Liquid crystal composition comprising the following compounds was prepared:

| | |
|---|---|
| 5-H2B(F)—CF3 | 5.0% |
| 3-H2BB(F)—CF3 | 5.0% |
| 3-HB(F)2B(F)—OCF3 | 5.0% |
| 5-HB—CL | 5.0% |
| 7-HB—CL | 5.0% |
| 4-HHB—CL | 10.0% |
| 5-HHB—CL | 5.0% |
| 3-HHB(F,F)—F | 10.0% |
| 3-HBB(F,F)—F | 15.0% |
| 5-HBB(F,F)—F | 15.0% |
| 3-H2BB(F,F)—F | 10.0% |
| 5-H2BB(F,F)—F | 10.0% |

Characteristics of the composition were determined and the results were as follows:

$T_{NI}$=63.9° C.

$T_{SN}$<-30° C.

η20=24.1 mPa·s

Δn=0.109

Δε=7.7

$V_{th}$=1.76 V

VHR=98.5%

EXAMPLE 6

Liquid crystal composition comprising the following compounds was prepared:

| | |
|---|---|
| 5-H2B(F)—CF3 | 10.0% |
| 3-H2BB(F)—OCF3 | 10.0% |
| 3-HHB(F,F)—F | 10.0% |
| 3-H2HB(F,F)—F | 10.0% |

-continued

| | |
|---|---|
| 4-H2HB(F,F)—F | 8.0% |
| 5-H2HB(F,F)—F | 10.0% |
| 3-HH2B(F,F)—F | 10.0% |
| 3-HBB(F,F)—F | 10.0% |
| 5-HBB(F,F)—F | 9.0% |
| 3-HHEB(F,F)—F | 10.0% |
| 3-HBEB(F,F)—F | 3.0% |

Characteristics of the composition were determined and the results were as follows:

$T_{NI}$=64.7° C.
$T_{SN}$<-30° C.
$\eta 20$=26.7 mPa·s
$\Delta n$=0.086
$\Delta \epsilon$=9.0
$V_{th}$=1.53 V
VHR=98.7%

EXAMPLE 7

Liquid crystal composition comprising the following compounds was prepared:

| | |
|---|---|
| 3-H2B(F)—CF3 | 5.0% |
| 3-H2H2B(F,F)—CF3 | 5.0% |
| 7-HB(F,F)—F | 4.0% |
| 3-H2HB(F,F)—F | 12.0% |
| 4-H2HB(F,F)—F | 10.0% |
| 5-H2HB(F,F)—F | 10.0% |
| 3-HHB(F,F)—F | 10.0% |
| 4-HHB(F,F)—F | 5.0% |
| 3-HH2B(F,F)—F | 15.0% |
| 3-HBB(F,F)—F | 12.0% |
| 5-HBB(F,F)—F | 6.0% |
| 3-HH2BB(F,F)—F | 6.0% |

Characteristics of the composition were determined and the results were as follows:

$T_{NI}$=71.5° C.
$T_{SN}$<-20° C.
$\eta 20$=27.6 mPa·s
$\Delta n$=0.084
$\Delta \epsilon$=8.5
$V_{th}$=1.61 V
VHR=98.6%

EXAMPLE 8

Liquid crystal composition comprising the following compounds was prepared:

| | |
|---|---|
| 3-H2H2B(F)—OCF3 | 10.0% |
| 3-H2BB(F)—CF3 | 4.0% |
| 3-H2HB(F,F)—F | 10.0% |
| 3-HHB(F,F)—F | 10.0% |
| 5-HHB(F,F)—F | 10.0% |
| 3-HH2B(F,F)—F | 10.0% |
| 5-HH2B(F,F)—F | 10.0% |
| 3-HBB(F,F)—F | 10.0% |
| 3-HHEB(F,F)—F | 10.0% |
| 2-HHB(F)—F | 2.0% |
| 3-HHB(F)—F | 2.0% |
| 5-HHB(F)—F | 2.0% |
| 4-H2BB(F)—F | 5.0% |
| 3-HH-4 | 5.0% |

Characteristics of the composition were determined and the results were as follows:

$T_{NI}$=89.7° C.
$T_{SN}$<-30° C.
$\eta 20$=24.6 mPa·s
$\Delta n$=0.084
$\Delta \epsilon$=7.8
$V_{th}$=1.90 V
VHR=98.5%

As the examples of the liquid crystal compositions of the present invention, the followings can be mentioned:

COMPOSITION EXAMPLE 1

| | |
|---|---|
| 3-H4B(F)—CF3 | 5.0% |
| 3-H2H2B(F,F)—OCF3 | 5.0% |
| 5-H2H2B(F,F)—OCF3 | 5.0% |
| 3-H2HB(F,F)—F | 10.0% |
| 5-H2HB(F,F)—F | 10.0% |
| 3-HHB(F,F)—F | 10.0% |
| 3-HH2B(F,F)—F | 12.0% |
| 5-HH2B(F,F)—F | 8.0% |
| 3-HBB(F,F)—F | 14.0% |
| 5-HBB(F,F)—F | 8.0% |
| 3-HHEB(F,F)—F | 10.0% |
| 2-HHBB(F,F)—F | 3.0% |

COMPOSITION EXAMPLE 2

| | |
|---|---|
| 5-HB(F)2B(F)—OCF3 | 10.0% |
| 3-HB(F)2B(F,F)—OCF3 | 5.0% |
| 7-HB(F,F)—F | 3.0% |
| 3-H2HB(F,F)—F | 12.0% |
| 4-H2HB(F,F)—F | 10.0% |
| 3-HHB(F,F)—F | 6.0% |
| 5-HHB(F,F)—F | 4.0% |
| 3-HH2B(F,F)—F | 15.0% |
| 5-HH2B(F,F)—F | 12.0% |
| 3-HBB(F,F)—F | 10.0% |
| 5-HBB(F,F)—F | 5.0% |
| 3-H2BB(F,F)—F | 8.0% |

COMPOSITION EXAMPLE 3

| | |
|---|---|
| 3-H2B(F)—CF3 | 5.0% |
| 3-H2BB(F)—OCF3 | 10.0% |
| 3-HHB(F,F)—F | 10.0% |
| 4-HHB(F,F)—F | 5.0% |
| 5-HHB(F,F)—F | 5.0% |
| 3-HBB(F,F)—F | 16.0% |
| 5-HBB(F,F)—F | 14.0% |
| 3-HH2B(F,F)—F | 8.0% |
| 4-HH2B(F,F)—F | 5.0% |
| 5-HH2B(F,F)—F | 7.0% |
| 3-HH2B(F)—F | 5.0% |
| 5-HH2B(F)—F | 5.0% |
| 5-HB(F)BH-3 | 5.0% |

COMPOSITION EXAMPLE 4

| | |
|---|---|
| 3-H4B(F)—CF3 | 5.0% |
| 3-H2H2B(F,F)—OCF3 | 10.0% |
| 3-HB(F)2B(F,F)—OCF3 | 10.0% |
| 3-H2HB(F,F)—F | 10.0% |
| 4-H2HB(F,F)—F | 8.0% |
| 5-H2HB(F,F)—F | 8.0% |
| 3-HH2B(F,F)—F | 10.0% |
| 5-HH2B(F,F)—F | 10.0% |

-continued

| | |
|---|---|
| 3-HBB(F,F)—F | 14.0% |
| 5-HHB—OCF3 | 5.0% |
| 3-HH2B—OCF3 | 5.0% |
| 5-HH2B—OCF3 | 5.0% |

We claim:

1. A liquid crystal composition comprising, as a first component, 3 to 50% by weight of at least one compound selected from the group consisting of the compounds expressed by any one of formulas (I-1) to (I-4)

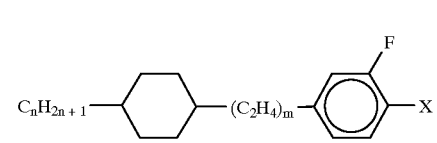
(I-1)

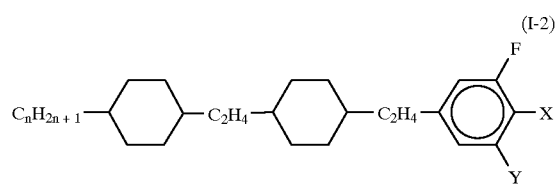
(I-2)

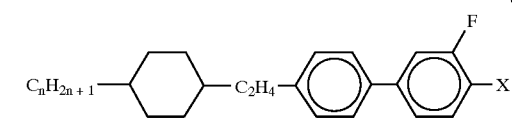
(I-3)

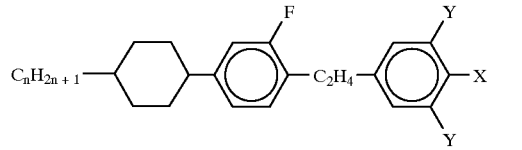
(I-4)

and as a second component, 50 to 97% by weight of at least one compound selected from the group consisting of the compounds expressed by any one of formulas (II-1) to (II-5)

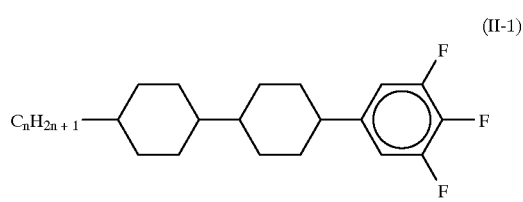
(II-1)

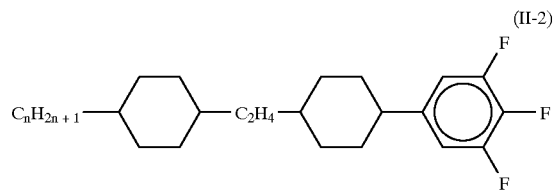
(II-2)

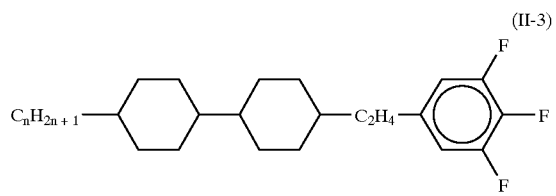
(II-3)

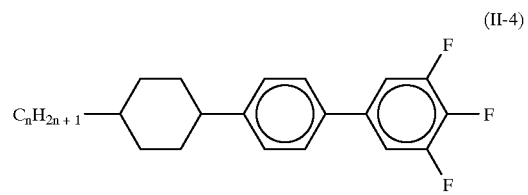
(II-4)

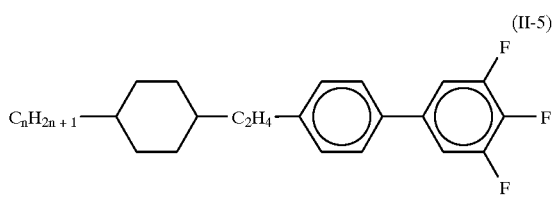
(II-5)

where in each of the formulas shown above, X represents $CF_3$ or $OCF_3$, each Y independently represents hydrogen atom or fluorine atom, m is 1 or 2, and n is an integer of 1 to 10.

in each of the formulas shown above, X represents $CF_3$ or $OCF_3$, Y represents or Ys independently with each other represent hydrogen atom or fluorine atom, m is 1 or 2, and n is an integer of 1 to 10.

2. The liquid crystalline composition according to claim 1 wherein the total amount of the first component and the second component is 60 to 100% by weight based on the total amount of the liquid crystal composition.

3. The liquid crystal composition according to any one of claim 1 wherein the liquid crystal composition further comprises at least one compound expressed by formula (III)

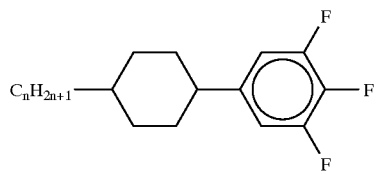
(III)

wherein n is an integer of 1 to 10.

4. The liquid crystal composition according to any one of claims 1 wherein the liquid crystal composition further comprises at least one compound expressed by formula (IV-1) or (IV-2)

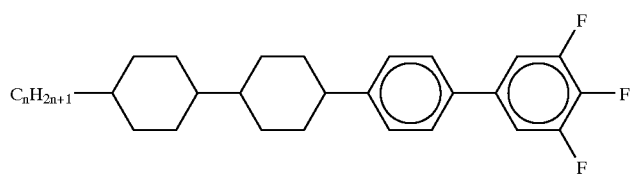

(IV-1)

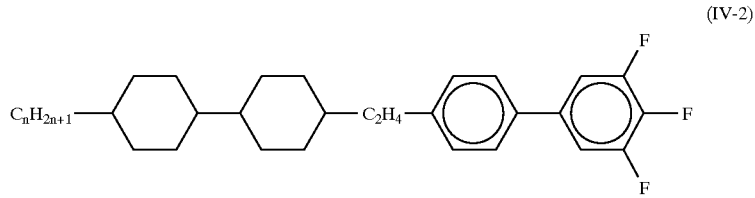

(IV-2)

wherein n is an integer of 1 to 10.

5. The liquid crystal composition according to any one of claims 1 wherein the liquid crystal composition further comprises at least one compound expressed by formula (V-1) or (V-2)

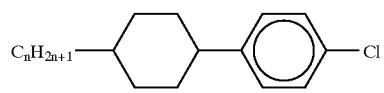

(V-1)

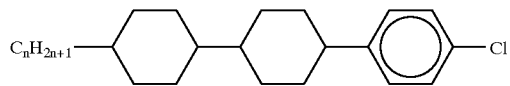

(V-2)

wherein n is an integer of 1 to 10.

6. The liquid crystal composition according to any one of claims 1 to 6 wherein the liquid crystal composition further comprises at least one compound expressed by formula (VI-1) or (VI-2) wherein n is an integer of 1 to 10.

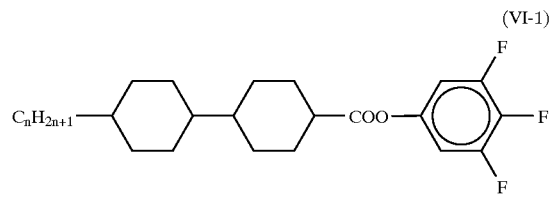

(VI-1)

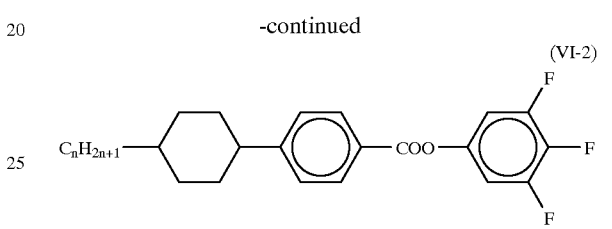

(VI-2)

7. A liquid crystal display device comprising a liquid crystal composition defined in claim 1.

8. A liquid crystal display device comprising a liquid crystal composition defined in claim 2.

9. A liquid crystal display device comprising a liquid crystal composition defined in claim 3.

10. A liquid crystal display device comprising a liquid crystal composition defined in claim 4.

11. A liquid crystal display device comprising a liquid crystal composition defined in claim 5.

12. A liquid crystal display device comprising a liquid crystal composition defined in claim 6.

13. The liquid crystal composition according to claim 1 wherein the first component is at least one compound selected from the group consisting of compounds expressed by any one of the formulas (I-2) to (I-4).

* * * * *